United States Patent [19]

Sclan et al.

[11] Patent Number: 5,082,446
[45] Date of Patent: Jan. 21, 1992

[54] METHOD FOR THE ASSESSMENT OF SEVERE DEMENTIA

[76] Inventors: Steven G. Sclan, 10 Waterside Plaza, Apt. #30B; Barry Reisberg, 20 Waterside Plaza #7K, both of New York, N.Y. 10010

[21] Appl. No.: 537,921

[22] Filed: Jun. 12, 1990

[51] Int. Cl.⁵ ............................................. G09B 19/00
[52] U.S. Cl. ................................... 434/236; 434/258
[58] Field of Search ............................... 434/258, 236

[56] References Cited

PUBLICATIONS

J. de Ajuriaguerra et al., "Concerning Some Problems Posed by the Functional Deficiency of The Aged Afflicted With Degenerative Senile Dementia", 1964, Cortex vol. I pp. 232-256.
Uzgiris & Hunt, Assessment in Infancy Ordinal Scales of Psychological Development, 1975, pp. 12, 48-50, 61, 144.
Reisberg et al, Senile Dementia of the Alzheimer Type: Diagnostic & Differential Diagnostic Features With Special Reference to Functional Assessment Staging, 1985, p. 30.
Tests & Measurements in Child Development: Handbook II, Jossey-Bass Publishers, 1976 pp. 33-36.
Scale I: The Development of Visual Pursuit and the Permanence of Objects, pp. 151-225.
Brazelton, Neonatal Behavioral Assessment Scale, SIMP publishers, 1973, pp. 4-61.

Primary Examiner—Richard J. Apley
Assistant Examiner—Karen A. Richard
Attorney, Agent, or Firm—Gottlieb, Rackman & Reisman

[57] ABSTRACT

A method for the cognitive assessment of adult patients with severe dementia. The method proceeds by adapting cognitive assessment tests for infants to the special requirements of such patients.

3 Claims, No Drawings

METHOD FOR THE ASSESSMENT OF SEVERE DEMENTIA

BACKGROUND OF THE INVENTION

This invention relates to methods for cognitive testing. In particular it relates to such testing for dementia patients with very severe cognitive impairment.

There are currently no psychometric measures or rating scales which permit a detailed description of the mental abilities of dementia patients having very severe cognitive impairment. Consequently, cognitive capacities in, for example, the hundreds of thousands of such patients in nursing homes, are currently not assessed. The method of this invention provides a way to generate cognitive test procedures for dementia patients.

According to a recent demographic report (Weiler, P. G. (1987), "The Public Health Impact of Alzheimer's Disease", *American Journal of Public Health*, Vol. 77(9), pp. 1157-1158) more than half of the current U.S. population will reach the age of 75 years and one quarter will reach the age 85 years. The prevalence of severe dementia in those over the age of 85 could be as high as 25%. (Cross & Gurland, B. (1986), The Epidemiology of Dementing Disorders, Contract Report, U.S. Office of Technology Assessment). For those between the ages of 75-85 years severe dementia occurs as frequently as myocardial infarct and more frequently than stroke (Oxman, T. E. (1987), Alzheimer's Disease: Molecular Biology, Society Treatment, *Psychiatric News*, July 3 (pp. 5-7)).

There is a lack of information regarding the cognitive capacities of dementia patients with severe and, especially, very severe cognitive impairment. It is becoming increasingly clear that this information is very important. For example, it is during these more advanced states that institutionalization and pharmacologic intervention often become unavoidable. Consequently, the proper identification of useful pharmacologic intervention modalities and their side effects necessitates improved measures of the cognitive status of these severely and very severely impaired Alzheimer's Disease (AD) patients.

A more comprehensive evaluation of patients at these stages will also result in useful information for caregivers. Specifically, family members frequently ask whether or not the patient "knows" them (i.e., recognizes who they are) or knows they are present at the bedside. This is of more than academic interest because the amount of attention that patients receive in their residential home or institutional setting may be dependent upon the caregiver's notion of the patient's ability to relate to others in the environment. Another impetus for the cognitive assessment of severely impaired patients comes from the Federal Government's Omnibus Budget Act of 1987 (U.S. Code Congressional & Administrative News, 1988) requiring that nursing homes prepare written plans describing their patients' medical, psychological and social conditions and needs. A more detailed assessment of severe and very severely cognitively impaired AD patients' cognitive status may allow for more complete documentation of the psychological condition and for provision of information that could be used in generating rehabilitative procedures that are matched to individual needs and abilities. Despite these needs, prior to the present invention no methods were developed for providing such cognitive test procedures and consequently, the appropriate psychometric measures and rating scales were not available.

SUMMARY OF THE INVENTION

The invention is based on the theory that in order to evaluate the cognitive capacities of severely impaired dementia patients one needs to assess internal mental structure using non-verbal measures that resemble a normal but less developed stage of cognition than would normally be applied to persons of these ages.

One major reason for the difficulties in evaluating the cognitive status of severely impaired dementia patients is the gradual loss of language and speech ability (i.e., dysphasia or aphasia). Another reason for the impediment in evaluating the cognitive status of severely impaired dementia patients is the unique mode of dissolution of higher mental thought processes in dementia. This decay of higher cognitive function in dementia appears to represent a reversal of those stages of cognitive development that are known from studies of infants and young children.

We have unexpectedly discovered that both cognitive and functional deterioration in the most common form of dementia (AD) resembles a reversal of the development of these acquisitions in normal infants and children. We have in addition, invented a method whereby the mental function in dementia patients with very severe cognitive impairment can be assessed using measures analogous to those previously applied only to infants and small children.

It is an object of the present invention to provide a method for the modification of test procedures based on Piagetian theory developed for use with infants and small children that results in test procedures effective in the cognitive assessment of adult persons with severe dementia.

It is a further object of the present invention to provide tests effective in the cognitive assessment of adult persons with severe dementia.

It is a further object of the present invention to provide such tests based on specialized infant and neo-nate measures such as the Einstein Scales of Sensorimotor Development (Escalona, S. & Corman, H. (1969), Albert Einstein Scales of Sensorimotor Development, New York: Dept. of Psychiatry, Albert Einstein) and the Brazelton Neonatal Assessment Scale (Brazelton, T. B. (1973), Neonatal Behavioral Assessment Scale, *Clinics in Developmental Medicine*, No. 50).

It is a still further object of the present invention to provide tests effective in the cognitive assessment of adult persons with severe dementia based on existing cognitive assessment procedures for infants and small children.

DETAILED DESCRIPTION OF A PREFERRED EMBODIMENT

In accord with the present invention, a measure was derived from the earliest stage of cognitive development (birth to age 2 in normal infancy) as hypothesized by Piaget and used to assess severely demented patients using this technique. The specific scales that have been modified for use with adult AD patients were selected from the Ordinal Scales of Psychological Development (OSPD; Uzgiris & Hunt, 1975).

The inventors have unexpectedly discovered that with the modification of the present invention the OSPD can be used with the elderly (and other adult) population. The method of the present invention comprises modifications to test measures and procedures which have been previously utilized for infants and small children.

Infants are fundamentally different from patients with dementia. These fundamental differences and evident dissimilarities are apparently the reason why infant assessments have not been adapted in the past to dementia patients. Among the fundamental differences are cognitive, motor and behavioral differences. Cognitively, infants display curiosity (i.e., they attend to, look for and reach out for cognitive stimulation) but dementia patients avoid stimulation unless specifically engaged. Behaviorally, infants cry but dementia patients generally do not. Also, the emotional repertoire of infants is much broader in general than that of dementia patients. In terms of motor capacity, infants crawl but dementia patients do not. Also, dementia patients frequently develop contractures (i.e., physiologic and neurologic changes which limit their motion).

The above fundamental differences—in cognition, affect and motor behavior—render the unmodified use of infant tests for dementia patients uninterpretable, misleading or, in some instances, impossible to administer. Accordingly, we have discovered processes by which infant tests can be adapted for use in dementia patients. The principles behind these processes require (a) selecting a test for infant or neo-nate cognitive development that is relevant for the cognitive assessment of patients with severe dementia; and (b) modifying the test in accordance with the fundamentally different cognitive, affective and motor capacities and status of dementia patients from that of infants.

Specifically, the first stage of the method entails the elimination of inappropriate tasks. Tasks ar eliminated which are beyond the motor capacities of severely demented patients due to complex neurologic/physiologic changes accompanying severe dementia, such as contractures or common cardiovascular complications. For example, the method requires the elimination of tasks requiring fine motor coordination or tasks that require independent ambulatory ability or other motor skills that are beyond the capacities of these patients because of complex neurologic or physiologic changes accompanying severe dementia.

The next stage of the method entails the substitution of new stimulus objects. Infants attend to toys and other stimulus objects because of their novel cognitive characteristics and, because of their intrinsic curiosity, infants attempt to manipulate these objects in some manner—these behaviors are severely compromised in adult dementia patients. The method provides for the substitution of new stimulus objects for the patients so that they will attempt the task (e.g., reaching for a photograph of a family member, a drinking cup or other object such as a mouth swab which may have been relevant in the patient's adult experience or is functionally relevant for their current domiciliary setting). These stimulus objects would be used in place of a doll, a building block or other toys which are not useful stimuli for dementia patients.

The next stage of the method calls for the modification of administration procedures. Actual administrative procedures must be changed because of the physical and environmental limitations of severely impaired dementia patients. For example, bringing stimulus objects for certain tasks into view of a patient whose eyesight is limited because of cataracts; bringing into reach stimulus objects for certain tasks because the patient is unable to ambulate—walk or even crawl—to the object; allowing for more repetitions of the item because of attentional deficits.

The final stage of the method calls for the modification of scoring methodology. Scoring methodology must be altered because of physical limitations of dementia patients. For example, giving full or partial credit to a patient who only partially reaches out for an object because of arthritis or stroke related disability; giving credit to a patient who has difficulty manipulating objects because of physical disability (e.g., arthritis or contractures).

As an example of the present invention, the technique was used with a measure that was previously developed for evaluation of the earliest stage of cognitive development (birth to age 2 in normal infancy) as hypothesized by Piaget. The specific measure chosen was a set of subscales from the Ordinal 16 Scales of Psychological Development (OSPD; Uzgiris & Hunt, 1975). To our knowledge, the OSPD have never been used with any elderly (or other adult) population. As enumerated above, modifications included elimination of certain tasks, substitution of more appropriate test stimuli and changes in administration and scoring of some of the items. This new evaluation instrument was then used to assess severely demented patients. Specific examples of modified test items include the following:

SCALE #1

Visual Pursuit and Object Permanence

1. Can the patient secure a partially hidden object?

Breakdown of Coordination Between Visual Following and Reaching a. Location: At this point, the patient must be in a sitting position, either in a chair, a wheelchair or sitting propped up in bed. A working surface must be available—either a table, bed table or even part of the patient's bed.

b. Materials: Any object which the patient demonstrates an interest in by looking at it and reaching for it (can use objects from the patient's bedside, photographs of family members, etc.). A dark handkerchief is used as a cover or screen.

c. Directions: For this test there is a difference in administration. It is that allowances are made for attentional and motivational deficits in elderly dementia patients. First, observe that the patient looks at the object and attempts to reach for it. If the patient is, at first, not interested in the object, then the object is used to attract the patient's attention (by dangling it or waving it in front of the patient). It is important that the patient see the object and attempt to reach for it before it is placed under the screen. Once the patient tries to reach for the object it is taken and placed on the working surface and covered with the screen in such a way that a small portion remains visible. This can be repeated 3-4 times.

d. Scoring: (1 point) - Patient attempts and/or does, in fact, obtain the object by pulling it out from under the screen or by removing the screen. The patient is given credit for attempting to reach for the object. It is frequently impossible for severely demented patients to actually obtain the object because of various physical limitations (e.g., contractures, paralysis).

(0 point) - Patient reacts to loss (cries, grunts, talks, agitated), but does not attempt to reach for it once it is partially covered.

2. Can the patient secure an object hidden under a single screen?

Loss of Limited Persistence of Representational Central

Processes and Destablization of Object Permanence a. Location: At this point, the patient must be in a sitting position, either in a chair, a wheelchair or sitting propped up in bed. A working surface must be available—either a table, bed table or even part of the patient's bed.

b. Materials: This involves a substitution of new objects. Items that may have been relevant to the patient in the past or items that are currently functionally relevant are used as stimulus objects. Any object which the patient demonstrates an interest in by looking at it and reaching for it (can use small dolls or stuffed animals or objects from the patient's bedside, photographs of family members, etc.). A dark handkerchief is used as a cover or screen.

c. Directions: Allowances are made for attentional and motivational deficits in elderly dementia patients. (Modifications of Administrative Procedures). First, observe that the patient looks at the object and attempts to reach for it. If the patient is, at first, not interested in the object, then the object is used to attract the patient's attention (by dangling it or waving it in front of the patient). It is important that the patient see the object and attempt to reach for it before it is placed under the screen. Once the patient tries to reach for the object it is taken and placed on the working surface and covered completely with a screen. This can be repeated 3 times.

d. Scoring: The patient is given credit for attempting to reach for the object. Moreover, another difference is that credit is given for an attempt after several trials. This latter change is made because severely demented patients may not be as curious or motivated as small children or infants.

Modification of Scoring Procedures (1 point) - Patient attempts and/or does, in fact, obtain the object even after repeated trials.

(0 point) - Patient looses interest in the object once it is covered.

(0 point) - Patient reacts to loss but does not attempt to obtain the object from under the screen.

SCALE #2

Means - Ends

1. Does the patient engage in any type of autogenic (i.e., self-stimulatory) activity?

Breakdown of Combined Use of 1 Behavior Pattern as a

"Means" With Another As "End" or "Goal"

a. Location: The patient may be supine, in bed, or seated in a wheelchair or any other chair or propped up in bed.

b. Materials: None c. Directions: the examiner (E) observes whether or not the patient engages in any self-stimulatory behavior. Examples of autogenic activity include continual handwatching while moving hands or pill-rolling, consistent fumbling of clothes or bedclothes with hands, putting fingers in mouth, etc.

d. Scoring: Allowances are made for more of a variety of movements or vocalizations on the part of the severely demented patient. Thus, the difference in scoring is that any sterotypic, self-stimulatory behavior is scored as "+".

Modification of Scoring
(1 point) - Self-stimulatory behavior is observed
(0 point) - no self-stimulatory behavior is observed

SCALE #4

Spatial Relations

1. Can the patient indicate the absence and/or location of a familiar person or place?

Decreasing Ability to Represent Familiar Objects in Familiar Space a. Location: The patient may be supine, in bed, or seated in a wheelchair or any other chair or propped up in bed.

b. Materials: None c. Directions: The emphasis is upon spatial location and orientation rather than familiar persons alone. Thus, the patient sees the aide leave the room and sees the direction in which the aide walks when he or she leaves the room. Additionally, the Examiner can ask the patient to point to where a certain room or facility is located. (Modification of Administration). The Examiner asks the relative or aide who is in the room with the patient to leave the room and go to another room or location in close proximity to the patient and E. The patient must see the aide or relative leave the room and go towards the new room or location. Once the relative or aide is in place, the Examiner asks the patient to identify who left the room and asks the patient to point where the person is.

Another possibility is for the Examiner to ask the patient to point to and/or tell where certain key nursing home locations (e.g., dining area, nurse's station, day room) are to be found.

Scoring:

(1 point) - The patient correctly names the person who just left the room and actually goes to that person.
(1 point) - The patient correctly names the person who just left the room and either correctly points or correctly says where that person is. (Modification has been made for possible use of higher order language (if it occurs) and for possible inability to ambulate.) (1 point) - Patient confuses person who left the room (but states some name) with another person who is present but correctly points or correctly says where the person is. (Modification has been in the form of a new alternative response —what is of most importance is the knowledge that someone left the room and in what general direction a person can be found.)

(0 point) - Patient does not seem to comprehend the question or the request.

(0 point) - Patient incorrectly names or confuses the person with someone who is not present or points incorrectly.

(0 point) - Patient does not respond.

SCALE #5

Schemes for Relating to Objects

1. Does the patient show (but not give) various objects to the examiner (suggesting the beginning of a shared experience)?

Advanced Awareness of the Social Significance of Objects in the Environment a. Location: The patient may be supine, in bed, or sitting in a wheelchair or a regular chair. The patient could also be propped up in bed.

b. Materials: Objects such as flowers, loose papers, drinking cup, a photograph or anything else that is in the room or home of the patient.

c. Directions: The Examiner waits for a time to ascertain whether or not the patient will spontaneously initiate an interpersonal experience. (Modification of Administration). The Examiner notes whether or not the patient spontaneously shows the Examiner any objects or personal belongings. If the patient does not spontaneously show anything to the Examiner, then Examiner presents various objects to the patient, one at a time, and observes the patient's actions. This can be repeated with 3-4 different objects.

d. Scoring: The Examiner must make allowances for difficulties that dementia patients may have communicating to others (e.g., speech difficulties, movement limitations). (Modifications of Scoring).

(1 point) - The patient shows 1 or more objects to the Examiner in a manner suggesting social interaction or the beginning of a shared social experience. This action is ascertained by noting if the patient extends the hand holding the object in the direction of another person or actually brings 1 object over to another person. The patient may also bring an object of his/her own to the Examiner or another person.

(1 point) - The patient spontaneously names an object or a part of an object immediately after being presented with it or after a period of examining it.

(1 point) - The patient introduces spouse or caregiver or aide to Examiner.

(1 point) - The patient shows pictures of family or some favored object to the Examiner.

(1 point) - The patient spontaneously begins to ask E about the exam.

(1 point) - The patient demonstrates to the Examiner or to someone else in the immediate vicinity a socially appropriate action in relation to the object.

(0 point) - The patient drops or throws objects, repeatedly, in order to attract and keep the attention of others in the environment.

We discovered that these modified procedures appear to be useful in the assessment of persons with severe and previously untestable dementia. Table 1 shows the obtained scores for each of 20 severely impaired patients on 5 scales of the OSPD.

TABLE 1

Individual OSPD[f] Scale Scores and their Association to Progressive-Clinically Assessed Functional Status (FAST)
(Patients with Clinically Diagnosed Alzheimer's Disease)
[f]Ordinal Scales of Psychological Development (OSPD)

| Subject No. | FAST Stage | Object Permanence** r—0.72 | Means-Ends** r—0.78 | Casuality** r—0.6 | Spatial Relations** r—0.78 | Schemes* r—0.65 |
|---|---|---|---|---|---|---|
| 1 | 6b | 14 | 13 | 6 | 11 | 10 |
| 2 | 6c | 13 | 12 | 6 | 11 | 3 |
| 3 | 6e | 8 | 10 | 4 | 7 | 5 |
| 4 | 6e | 5 | 5 | 1 | 6 | 5 |
| 5 | 6e | 1 | 4 | 0 | 4 | 0 |
| 6 | 7a | 13 | 13 | 6 | 11 | 9 |
| 7 | 7a | 2 | 4 | 1 | 7 | 2 |
| 8 | 7b | 4 | 3 | 1 | 5 | 2 |
| 9 | 7b | 1 | 3 | 1 | 4 | 2 |
| 10 | 7b | 1 | 1 | 1 | 1 | 0 |
| 11 | 7b | 1 | 0 | 0 | 5 | 0 |
| 12 | 7b | 1 | 3 | 1 | 4 | 2 |
| 13 | 7c | 1 | 4 | 1 | 6 | 2 |
| 14 | 7c | 4 | 3 | 1 | 5 | 2 |
| 15 | 7c | 2 | 3 | 1 | 4 | 2 |
| 16 | 7d | 3 | 3 | 2 | 3 | 2 |
| 17 | 7d | 1 | 3 | 1 | 1 | 2 |
| 18 | 7d | 1 | 1 | 1 | 4 | 1 |
| 19 | 7e | 1 | 1 | 1 | 3 | 0 |
| 20 | 7f | 1 | 0 | 0 | 1 | 0 |

*$p < .01$; **$p < .001$

2. Does the patient spontaneously name objects and-/or indicate a definite awareness of the social significance of objects in the environment?

Advanced Awareness of the Social Significance of Objects in the Environment a. Scoring: The focus of this task is to indicate to the Examiner that the patient still possesses the fundamental ability to initiate and maintain a minimal social relationship with another in the environment. In terms of differences in scoring, the Examiner must make allowances for difficulties that dementia patients may have communicating to others (e.g., speech difficulties, movement limitations)

Modification of Scoring

These patients were also evaluated and staged according to severity of functional impairment on the FAST staging measure. (Reisberg, B., Ferris, S. & deLeon, M. (1985), Senile dementia of Alzheimer type: Diagnostic and differential diagnostic features with special reference to functional assessment staging; In J. Traber & W. Gispen (Eds.), *Senile Dementia of the Alzheimer Type.* Berlin, Heidelberg: Springer-Verlag. Reisberg, B., Ferris, S. & Franssen, E. (1986). Functional degenerative stages in dementia of the Alzheimer's type appear to reverse normal human development; In C. Shagass, et al., (Eds.). *Biological Psychiatry* 1985 (Vol. 7, pp. 1319-1321), New York: Elsevier Science Pub. Co.)

It is clear from this data that responses can now be obtained from previously untestable severely impaired dementia patients using the method of this invention. These responses have strong relationships to previously described, independent, functional assessments of deterioration.

Clinical Advantages of the Assessment Procedures

This invention has accomplished the following:

1) allows for a more comprehensive appreciation of the mental capabilities of severe and very severe cognitively impaired dementia patients;

2) provides useful information to families and caregivers of these patients;

3) provides information that could be useful in generating appropriate activities for these patients that are better matched to individual needs and abilities;

4) improves clinical and research capacity to evaluate the benefit of psychopharmacologic intervention strategies for these patients;

5) improves the ability of research and health professionals to track and monitor the course of deterioration of persons with severe dementia.

We claim:

1. A process for the development of cognitive and psychological tests useful for the assessment of mental status in severely cognitively impaired dementia patients comprising the steps of
    a) selecting a full psychological test battery for infant cognitive development,
    b) eliminating tasks of said test battery beyond the physical capabilities of severely demented patients,
    c) substituting unfamiliar stimulus objects used in said test battery with already familiar or utilitarian stimulus objects relevant in the patient's adult experience,
    d) modifying examining procedures of said test battery to accommodate any physical limitations of dementia patients, and
    e) modifying scoring methodology of said test battery to adapt to the physical limitations of dementia patients.

2. The method of claim 1 wherein said step of modifying examining procedures comprises bringing stimulus objects into reach of the patient.

3. The method of claim 1 wherein said step of modifying scoring methodology comprises giving credit to a patient who only partially reaches for an object.

* * * * *